United States Patent

Bernauer et al.

[11] Patent Number: 4,482,739
[45] Date of Patent: Nov. 13, 1984

[54] CARBAMOYL ALKYLENE PHENYL UREAS

[75] Inventors: Karl Bernauer, Oberwil; Helmut Link, Basel; Harro Stohler, Binningen, all of Switzerland

[73] Assignee: Hoffmann-La Roche Inc., Nutley, N.J.

[21] Appl. No.: 493,855

[22] Filed: May 12, 1983

Related U.S. Application Data

[60] Division of Ser. No. 330,364, Dec. 14, 1981, Pat. No. 4,407,814, which is a continuation of Ser. No. 118,004, Feb. 4, 1980, abandoned, which is a continuation of Ser. No. 954,073, Oct. 24, 1978, abandoned.

[30] Foreign Application Priority Data

Oct. 28, 1977 [LU] Luxembourg .......................... 78407
May 19, 1978 [CH] Switzerland ......................... 5465/78
Sep. 6, 1978 [CH] Switzerland ......................... 9367/78

[51] Int. Cl.³ .......................................... C07C 127/19
[52] U.S. Cl. ...................................... 564/54; 564/53
[58] Field of Search ................................. 564/53, 54

[56] References Cited

U.S. PATENT DOCUMENTS 3,668,217 6/1972 Fujinami et al. ................. 548/314
3,690,863 9/1972 Gerike ............................ 564/53 X
4,234,736 11/1980 Bernauer et al. ........... 424/273 R X
4,358,606 11/1982 Lee et al. ....................... 564/56 X

FOREIGN PATENT DOCUMENTS 53-15373 2/1978 Japan .

Primary Examiner—Thomas A. Waltz
Attorney, Agent, or Firm—Jon S. Saxe; Bernard S. Leon; George M. Gould

[57] ABSTRACT

Imidazolidine derivatives of the formula

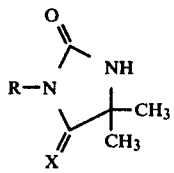

wherein X is oxygen or imino and R is one of the groups

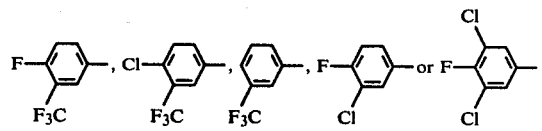

their preparation, use as antiandrogenically or schistosomicidally active agents, and corresponding pharmaceutical preparations, are described.

1 Claim, No Drawings

CARBAMOYL ALKYLENE PHENYL UREAS

This is a division of application Ser. No. 330,364, filed Dec. 14, 1981, now U.S. Pat. No. 4,407,814, which is a continuation of Ser. No. 118,004, filed Feb. 4, 1980, now abandoned, which is a continuation of Ser. No. 954,073, filed Oct. 24, 1978, now abandoned.

BRIEF SUMMARY OF THE INVENTION

The invention relates to imidazolidine derivatives of the formula

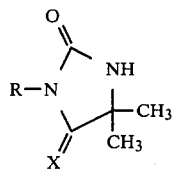

wherein X and R are as herein described.

In another aspect, the invention relates to a method of using the compounds of formula I as antiandrogenic agents, and to pharmaceutical compositions comprising the compounds of formula I.

In yet another aspect, the invention relates to urea derivatives of the formula

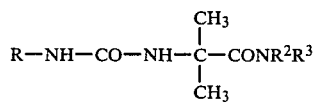

wherein R is one of the groups

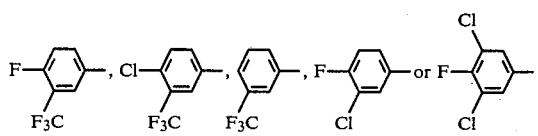

and $R^2$ and $R^3$ both are lower alkyl.

DETAILED DESCRIPTION OF THE INVENTION

The invention relates to imidazolidine derivatives of the formula

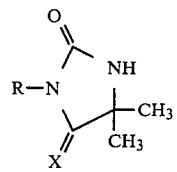

wherein X is oxygen or imino and R is

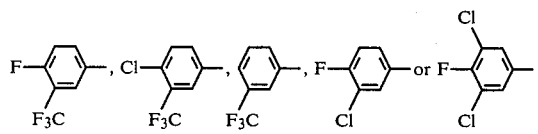

The imidazolidine derivates of formula I have valuable therapeutic properties, and can therefore be used as medicaments. The compounds of formula I are distinguished, for example, by antiandrogenic activity and can therefore be used as agents having an antiandrogenic action, especially in the treatment of diseases associated with an increased androgenic activity, such as, for example, acne, seborrhoea, hirsutism and adenoma of the prostate. Particularly preferred, antiandrogenically active compounds of formula I are those wherein X is oxygen. Among such compounds, 3-(3-chloro-4-fluoro-phenyl)-5,5-dimethylhydantoin is especially preferred. Those imidazolidine derivatives of formula I wherein R is one of the first four groups above are also schistosomicidally active and can thus be employed for the therapy and prevention of bilharziosis (schistosomiasis). Of these, preferred are those wherein X is oxygen. 3-(3-Trifluoromethyl-4-fluorophenyl)-5,5-dimethylhydantoin and 1-(3-trifluoromethyl-4-fluorophenyl)-5-imino-4,4-dimethyl-2-imidazolidinone are especially preferred because of their powerful schistosomicidal action.

The various imidazolidine derivatives of formula I can be prepared in accordance with the invention, as follows:

(a) to prepare a compound of formula I wherein X is oxygen, a compound of the formula

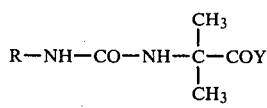

wherein R is as previously described and Y is $-OR^1$ or $-NR^2R^3$, wherein $R^1$ is hydrogen or lower alkyl, and $R^2$ and $R^3$ both are lower alkyl, is cyclized, or (b) to prepare a compound of formula I wherein X is imino, a compound of the formula

R—NCO III wherein R is as previousyl described, is reacted under anhydrous conditions with α-aminoisobutyronitrile, or (c) to prepare a compound of formula I wherein X is oxygen, a compound of the formula

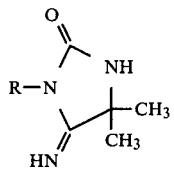

wherein R is as previously described, is subjected to hydrolysis.

Those novel starting compounds of formula II which are acid amides are also part of the invention.

Hereinafter, the various embodiments of the process in accordance with the invention for the preparation of the imidazolidine derivatives of formula I are illustrated in more detail.

Starting amides of formula II, that is, compounds II wherein $Y=NR^2R^3$, can be prepared by reacting a substituted benzhydroxamic acid of the formula

R—CONHOH IV wherein R is as previously described, with an azirine derivative of the formula

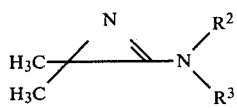

wherein $R^2$ and $R^3$ are as previously described.

The reaction proceeds successfully in an inert organic solvent, such as tetrahydrofuran, ether or dioxane, at room temperature and with slight warming, for example, to 50° C.

The starting esters of formula II, that is, compounds of formula II wherein $Y=OR^{10}$, wherein $R^{10}$ is lower alkyl, can be prepared by reacting a compound of the formula

   VI under anhydrous conditions with a compound of the formula

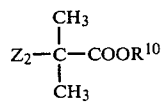   VII wherein R and $R^{10}$ are as previously described, and one of the symbols $Z_1$ and $Z_2$ is amino and the other is the isocyanate group —NCO.

This addition reaction can be carried out without the addition of solvents, that is, by means of a melt, or also by warming in an inert, anhydrous solvent, for example, tetrahydrofuran, ether, dioxane, benzene or toluene. The temperaure for the reaction is preferably in the range of about 0°–120° C. If the reaction is carried out as a melt, it must be noted that relatively high temperatures or relatively long reaction times had to cyclization and the formation of the corresponding hydantoin of formula I. In order to isolate a starting ester of formula II, the reaction should be interrupted in time, which can be accomplished, for example, by monitoring with thin-layer chromatography. However, it is preferable not to isolate the ester of formula II but to allow the reaction to proceed until the corresponding hydantoin of formula I is formed, as indicated hereinafter.

To prepare a carboxylic acid of formula II, that is, a compound of formula II wherein Y=hydroxyl, an amide of formula II can be dissolved in an inert organic solvent, for example, methanol or ethanol, and the solution can be treated with aqueous alkali, for example, caustic soda solution or caustic potash solution, at a temperature in the range of from room temperature to the boiling point of the reaction mixture. The corresponding carboxylic acid of formula II is obtained in the customary manner by neutralizing the carboxylic acid salt formed, for example, using a mineral acid.

The cyclization of the starting compounds of formula II leads to hydantoins of formula I, that is, compounds of formula I wherein X=oxygen. This cyclization is carried out, for example, under conditions of acid hydrolysis, preferably by treatment with an aqueous mineral acid, such as, aqueous hydrochloric acid. The hydrolysis of amides of formula II is advantageously carried out in an inert organic solvent, for example, tetrahydrofuran or dioxane, and at about room temperature. It is also possible to carry out the hydrolysis at higher temperatures, for example, up to the boiling temperature of the reaction mixture. The cyclization of esters or carboxylic acids of formula II is preferably carried out with a water-miscible solvent, such as, acetone, methyl ethyl ketone, tetrahydrofuran, dimethoxyethane or dioxane. A preferred agent for cyclization is 6-N aqueous hydrochloric acid and acetone in a weight ratio of 1:1. The reaction temperature is preferably the boiling temperature of the reaction mixture. However, it is also possible to use lower reaction temperatures, for example, up to room temperature, with correspondingly longer reaction times. The starting esters of formula II can also be cyclized by warming without solvents, that is, by means of a melt. The temperature for the melt reaction is preferably in the range of form about 100° to 200° C., in particular in the range of from about 120° to 160° C. According to a preferred embodiment, the cyclization is carried out utilizing the compounds of the above formulas VI and VII which can be used for the preparation of the starting esters of formula II, by choosing an adequate reaction time or reaction temperature. The reaction proceeds to the desired cyclization product, that is, the hydantoin of formula I, without isolating the esters of formula II intermediately formed. The reaction can be followed, for example, by thin-layer chromatography.

The anhydrous reaction in accordance with the invention of the isocyanate of formula III with α-aminoisobutyronitrile leads to imidazolidine derivatives of formula I wherein X is imino. The reaction can be carried out under the same conditions as the cyclization described above, using compounds of formulas VI and VII, that is, by means of a melt. It is also possible to obtain the imino derivative by heating the starting compounds with an ethereal solvent, for example, with dioxane or dimethoxyethane.

The hydrolysis of the starting compounds of formula Ia leads to corresponding hydantoins of formula I, that is, compounds of formula I wherein X=oxygen. The hydrolysis can be carried out, optionally with the addition of an inert solvent, by treatment with, for example, a mineral acid, such as, hydrochloric acid, at a temperature in the range of room temperature to the boiling point of the reaction mixture.

Some of the compounds of formula I are crystalline, solid substances which have a relatively good solubility in lower alkanols, such as, methanol or ethanol, in dimethylsulfoxide, dimethylformamide and hexamethylphosphoric acid triamide and, in some cases, also in chlorinated hydrocarbons, such as chloroform, methylene chloride and carbon tetrachloride, and are relatively sparingly soluble in ether, benzene and water.

As stated, the end products of formula I have an antiandrogenic action. This action can be demonstrated, for example, by the following test:

10 mg. per kg. of the preparation to be investigated, together with 0.5 mg per kg of testosterone propionate, are administered subcutaneously daily to each of a group of 5 male, sterilized rats over 7 days. Two control groups of 5 rats each received no treatment or only testosterone propionate, respectively. The decrease in weight of the ventral prostata and the seminal vesicle is a measure of the antiandrogenic action.

Table I below provides information on some test results.

TABLE I

| Compound | Ventral prostata mg | Seminal vesicle mg |
|---|---|---|
| Control | 7.6 ± 0.4 | 6.3 ± 0.5 |
| Testosterone propionate | 69.0 ± 3.9 | 47.0 ± 3.1 |
| 3-(3-Trifluoromethyl-4-chloro-phenyl)-5,5-dimethyl-hydantoin + testosterone propionate | 25.0 ± 1.0 | 23.0 ± 1.6 |
| Control | 8.0 ± 0.4 | 6.3 ± 0.4 |
| Testosterone propionate | 59.0 ± 2.0 | 42.0 ± 1.6 |
| 1-(3-Trifluoromethyl-4-chloro-phenyl)-5-imino-4,4-dimethyl-2-imidazolidinone + testosterone propionate | 29.0 ± 2.2 | 24.0 ± 0.6 |
| 3-(3-Trifluoromethyl-phenyl)-5,5-dimethyl-hydantoin + testosterone propionate | 35.0 ± 1.9 | 29.0 ± 1.4 |
| 3-(3-Trifluoromethyl-4-fluoro-phenyl)-5,5-dimethyl-hydantoin + testosterone propionate | 21.0 ± 1.0 | 18.0 ± 0.9 |
| Control | 14 ± 1 | 24 ± 2 |
| Testosterone propionate | 121 ± 13 | 100 ± 9 |
| 1-(3-Trifluoromethyl-4-fluoro-phenyl)-5-imino-4,4-dimethyl-2-imidazolidinone + testosterone propionate | 31 ± 4 | 30 ± 2 |
| Control | 22 ± 2 | 48 ± 4 |
| Testosterone propionate | 184 ± 8 | 145 ± 7 |
| 3-(3,5-Dichloro-4-fluoro-phenyl)-5,5-dimethyl-hydantoin + testosterone propionate | 72 ± 9 | 62 ± 3 |

The schistosomicidal action of the end products, defined above, can be demonstrated by the following test Mice are infected subcutaneously with 60 cercariae of *Schistosoma mansoni*. About 42 days after the infection, the animals are treated perorally once or (in an additional test) on 5 successive days with the compounds to be tested. 5-10 animals are use per compound and dosage (mg/kg). Ten untreated animals serve as the control. The autopsy is carried out 6 days or 2-3 weeks after conclusion of the treatment. Worm pairs in mesenteric veins, the portal vein and the liver are dissected out and counted. The percentage distribution of the worm pairs in mesenteric veins, the portal vein and the liver is calculated and the condition of the worms (living or dead) is recorded. The action of the preparation is manifested in an increased proportion of worms in the vessels of the liver and in the appearance of dead worms.

For the evaluation, the percentage proportion of living and dead worm pairs in the vessels of the liver both in infected, treated animals and in infected but untreated control animals is compared. The determination of the $VD_{50}$ (vermicidal dose 50%: the dose which kills 50% of the worm pairs) is carried out by the Probit method.

Some test results are summarized in Table II below:

TABLE II

| Compound | $VD_{50}$ mg/kg p.o. administered once | $VD_{50}$ mg/kg p.o. administered 5 times |
|---|---|---|
| 3-(3-Trifluoromethyl-4-fluoro-phenyl)-5,5-dimethyl-hydantoin | 47 | 15 |
| 3-(3-Trifluoromethyl-4-chloro-phenyl)-5,5-dimethyl-hydantoin | 59 | 29 |
| 3-(3-Trifluoromethyl-phenyl)-5,5-dimethyl-hydantoin | 60 | 32 |
| 3-(3-Chloro-4-fluoro-phenyl)-5,5-dimethyl-hydantoin |  | 68 |
| 1-(3-Trifluoromethyl-4-chloro-phenyl)-5-imino-4,4-dimethyl-2-imidazolidinone | 58 | 33 |
| 1-(3-Trifluoromethyl-4-fluoro-phenyl)-5-imino-4,4-dimethyl-2-imidazolidinone | 37 | 21 |

The toxic action in mice (observed after 24 hours) was likewise determined as can be seen from Table III below:

TABLE III

| Compound | $LD_{50}$ mg/kg p.o. |
|---|---|
| 3-(3-Trifluoromethyl-4-fluoro-phenyl)-5,5-dimethyl-hydantoin | 1250-2500 |
| 3-(3-Trifluoromethyl-4-chloro-phenyl)-5,5-dimethyl-hydantoin | 5000 |
| 3-(3-Trifluoromethyl-phenyl)-5,5-dimethyl-hydantoin | 625-1250 |
| 3-(3-Chloro-4-fluoro-phenyl)-5,5-dimethyl-hydantoin | 2500-5000 |
| 1-(3-Trifluoromethyl-4-chloro-phenyl)-5-imino-4,4-dimethyl-2-imidazolidinone | 312-625 |
| 1-(3-Trifluoromethyl-4-fluoro-phenyl)-5-imino-4,4-dimethyl-2-imidazolidinone | 312-625 |
| 3-(3,5-Dichloro-4-fluoro-phenyl)-5,5-dimethyl-hydantoin | 1250-2500 |

The compounds of formula I can be used as medicines, for example, in the form of pharmaceutical preparations which contain them mixed with a pharmaceutical organic or inorganic carrier material suitable for enteral or parenteral administration, such as, gelatin, lactose, starch, gum arabic, magnesium stearate, talc, vegetable oils, polyalkylene glycols, Vaseline and other similar carriers. The pharmaceutical preparations can be in the solid form, for example, as tablets or dragees, or in the liquid form, for example, as solutions, suspensions or emulsions. The pharmaceutical preparations can contain adjuvants, such as, preserving, stabilizing, wetting or emulsifying agents, salts for modifying the osmotic pressure or buffers. Therapeutically active substances can also be admixed.

Appropriate pharmaceutical dosage forms contain from about 10 to 500 mg. of a compound of formula I.

The dosage is chosen according to the requirements of the warm-blooded animal to be treated. The compounds of formula I can be administered, for example, in dosages from about 0.1 mg/kg. to about 50 mg/kg. p.o. daily.

Dosage forms which can be used as antiandrogenic agents appropriately contain from about 10 to 500 mg, preferably about 100 mg, of active substance. The dosage is, for example, from about 0.1 mg/kg to about 10 mg/kg p.o. daily, preferably about 1 mg/kg p.o. daily. This dose is appropriately administered daily for about 3-8 months, according to the condition of the patient.

Dosage forms which can be used as schistosomicidal agents appropriately contain from about 100 to 500 mg, preferably about 250 mg, of active substance. The dosage is, for example, from about 5 mg/kg to about 50 mg/kg p.o. daily, preferably 25 mg/kg p.o. daily. The foregoing amounts can be administered in a single dosage or in several subdivided dosages, depending on the requirements of the warm-blooded animal to be treated and the instructions of the expert. The dose to be utilized is appropriately administered on one day or on several successive days, according to the condition of the warm-blooded animal to be treated.

The Examples which follow further illustrate the invention. Unless otherwise stated, the temperatures are given in degrees Centigrade.

EXAMPLE 1

Preparation of 3-(3-chloro-4-fluoro-phenyl)-5,5-dimethylhydantoin 14.5 g. of 3-chloro-4-fluoroaniline and 17.2 g. of 2-isocyanate-2-methylpropionic acid methyl ester are melted at 140° and the melt is kept at this temperature for 6 hours. The N-[(3-chloro-4-fluoro-phenyl)-carbamoyl]-2-methylaniline methyl ester intermediately formed is not isolated. The 3-(3-chloro-4-fluoro-phenyl)-5,5-dimethylhydantoin obtained is crystallized from isopropanol/methanol/methylene chloride.

After drying under greatly reduced pressure at 55° for 16 hours, the product melts at 165°–166°.

Analysis: Calculated for $C_{11}H_{10}ClFN_2O_2$ (256.66): C 51.48, H 3.93, N 10.91, Cl 13.81% Found: C 51.51, H 3.78, N 11.11, Cl 13.92%

EXAMPLE 2

Preparation of N-[(3,5-dichloro-4-fluoro-phenyl)-carbamoyl]-2-methyl-alanine methyl ester 3-(3,5-dichloro-4-fluoro-phenyl)-5,5-dimethylhydantoin, which melts at 175°–176°, is obtained in the manner indicated in Example 1 from 3,5-dichloro-4-fluoro-aniline and 2-isocyanato-2-methylpropionic acid methyl ester and after crystallizing from ether/petroleum ether. The N-[(3,5-dichloro-4-fluorophenyl)-carbamoyl]-2-methylalanine methyl ester intermediately formed is not isolated.

Analysis: Calculated for $C_{11}H_9Cl_2FN_2O_2$ (291.11): C 45.39, H 3.12, N 9.62, Cl 24.36%; Found: C 45.55, H 3.19, N 9.57, Cl 24.58%

The following compound is obtained in the same manner: 3-(3-trifluoromethyl-4-fluoro-phenyl)-5,5-dimethylhydantoin; mp 111°–112°.

EXAMPLE 3

Preparation of 3-(3-trifluoromethyl-4-chlorophenyl)-5,5-dimethyl-hydantoin

A solution of 8.00 g. of N-[(3-trifluoromethyl-4-chloro-phenyl)-carbamoyl]-2-methylalanine methyl ester in 20 ml. of 6-N aqueous hydrochloric acid and 20 ml. of acetone are warmed on a steam bath for 2 hours and the mixture is then concentrated. The product which was precipitated is first recystallized from methylene chloride and then from methylene chloride/petroleum ether. After drying under greatly reduced pressure at 50° for 20 hours, 3-(3-trifluoromethyl-4-chloro-phenyl)-5,5-dimethylhydantoin of melting point 152°–153° is obtained.

Analysis: Calculated for $C_{12}H_{10}ClF_3N_2O_2$ (306.67): C 47.00, H 3.29, N 9.13% Found: C 46.89, H 3.23, N 8.93%

The following compound is obtained in the same manner: 3-(3-trifluoromethylphenyl)-5,5-dimethylhydantoin; mp 105°–106°.

The N-[(3-trifluoromethyl-4-chlorophenyl)-carbamoyl]-2-methylalanine methyl ester employed as a starting compound can be prepared as follows:

9.75 g. of 5-amino-2-chlorobenzotrifluoride and 7.15 g. of 2-isocyanato-2-methylpropionic acid methyl ester are melted a 80° and the melt is kept at this temperature for 30 minutes. The product which has crystallized out during this process is recrystallized from isopropanol/methylene chloride and dried under greatly reduced pressure at 50° for 20 hours. N-[(3-trifluoromethyl-4-chlorophenyl)-carbamoyl]-2-methylalanine methyl ester, which melts at 141°–142° is obtained.

Analysis: Calculated for $C_{13}H_{14}ClF_3N_2O_3$ (338.71): C 46.10, H 4.17, N 8.27% Found: C 46.17, H 4.14, N 8.26%

The N-[(3-trifluoromethylphenyl)-carbamoyl]-2-methylalanine ester used as a starting compound can be prepared in a similar manner (in the melt at 130° for 120 minutes).

EXAMPLE 4

Preparation of 1-(3-trifluoromethyl-4-chlorophenyl)-5-imino-4,4-dimethyl-2-imidazolidinone 14.5 g. of 3-trifluoromethyl-4-chlorophenyl-isocyanate and 5.5 g. of α-aminoisobutyronitrile are kept at 100° for 20 minutes. For purification, the viscous oil obtained is chromatographed on 500 g. of silica gel (particle size about 0.06–0.2 mm) using methylene chloride/methanol. The product obtained is crystallized from methylene chloride/petroleum ether. After drying under greatly reduced pressure at 50° for 15 hours, 1-(3-trifluoromethyl-4-chlorophenyl)-5-imino-4,4-dimethyl-2-imidazolidinone, which melts at 148°–149°, is obtained.

Analysis: Calculated for: $C_{12}H_{11}ClF_3N_3O$ (305.69): C 47.15, H 3.63, N 13.75, Cl 11.60% Found: C 47.11, H 3.66, N 13.84, Cl 11.86%

The following compound is prepared in the same manner: 1-(3-trifluoromethyl-4-fluoro-phenyl)-5-imino-4,4-dimethyl-2-imidazolidinone; Smp 92°–93° (from ether/n-pentane).

Analysis: Calculated for: $C_{12}H_{11}F_4N_3O$ (289.23): C 49.83, H 3.83, N 14.53% Found: C 49.69, H 3.48, N 14.18%

EXAMPLE 5

Preparation of 3-(3-trifluoromethyl-4-chlorophenyl)-5,5-dimethyl-hydantoin 61 mg. of 1-(3-trifluoromethyl-4-chlorophenyl)-5-imino-4,4-dimethyl-2-imidazolidinone are dissolved in 4 ml. of 0.1-N aqueous hydrochloric acid, and 2 ml. of water are added. The white needles which gradually precipitate are removed by filtration after 20 hours, washed with water and dried under greatly reduced pressure at 65° for 2 hours. 3-(3-trifluoromethyl-4-chlorophenyl)-5,5-dimethylhydantoin, which melts at 156°–157.5°, is obtained.

EXAMPLE 6

Preparation of tablets of the following composition:

| | |
|---|---|
| 3-(3-chloro-4-fluoro-phenyl)-5,5-dimethylhydantoin | 100.0 mg. |
| Lactose | 40.0 mg. |
| Maize starch | 34.0 mg. |
| Ethyl cellulose | 4.0 mg. |
| Talc | 1.8 mg. |
| Magnesium stearate | 0.2 mg. |
| | 180.0 mg. |

The 3-(3-chloro-4-fluoro-phenyl)-5,5-dimethylhydantoin is mixed with the lactose and the maize starch. The mixture is granulated with a solution of the ethyl cellulose in 16 ml. of methylene chloride. The granulate is dried at 40° and mixed with the talc and magnesium stearate, and the mixture is pressed into tablets.

| | |
|---|---|
| Weight of one tablet | 180 mg. |
| Active substance content of one tablet | 100 mg. |

EXAMPLE 7

Preparation of tablets of the following composition:

| | |
|---|---|
| 3-(3-Trifluoromethyl-4-fluoro-phenyl)-5,5-dimethylhydantoin | 250.0 mg. |
| Lactose | 100.0 mg. |
| Maize starch | 85.0 mg. |
| Ethyl cellulose | 10.0 mg. |
| Talc | 4.5 mg. |
| Magnesium stearate | 0.5 mg. |
| | 450.0 mg. |

The 3-(3-Trifluoromethyl-4-fluoro-phenyl)-5,5-dimethylhydantoin is mixed with the lactose and the maize starch. The mixture is granulated with a solution of the ethyl cellulose in 40 ml. of methylene chloride. The granulate is dried at 40° and mixed with the talc and magnesium stearate, and the mixture is pressed into tablets.

| | |
|---|---|
| Weight of one tablet | 450 mg. |
| Active substance content of one tablet | 250 mg. |

EXAMPLE 8

Preparation of capsules of the following composition:

| | |
|---|---|
| 3-(3-chloro-4-fluoro-phenyl)-5,5-dimethylhydantoin | 100.0 mg. |
| Lactose | 62.0 mg. |
| Maize starch | 12.0 mg. |
| Talc | 6.0 mg. |
| | 180.0 mg. |

The 3-(3-chloro-4-fluoro-phenyl)-5,5-dimethylhydantoin is homogeneously mixed with the lactose and the maize starch and the mixture is passed through a sieve machine and, after intermixing of the talc, filled into gelatin capsules

| | |
|---|---|
| Weight of the filling in the capsule | 180 mg. |
| Active substance content | 100 mg. |

EXAMPLE 9

Preparation of capsules of the following composition:

| | |
|---|---|
| 3-(3-Trifluoromethyl-4-fluoro-phenyl)-5,5-dimethylhydantoin | 250.0 mg. |
| Lactose | 155.0 mg. |
| Maize starch | 30.0 mg. |
| Talc | 15.0 mg. |
| | 450.0 mg. |

The 3-(3-Trifluoromethyl-4-fluoro-phenyl)-5,5-dimethylhydantoin is homogeneously mixed with the lactose and the maize starch. The mixture is passed through a sieve machine and, after intermixing of the talc, filled into gelatin capsules.

| | |
|---|---|
| Weight of the filling in the capsule | 450 mg. |
| Active substance content | 250 mg. |

We claim:

1. A compound of the formula $$R-NH-CO-NH-\underset{\underset{CH_3}{|}}{\overset{\overset{CH_3}{|}}{C}}-CONR^2R^3 \qquad IIa$$

wherein R is

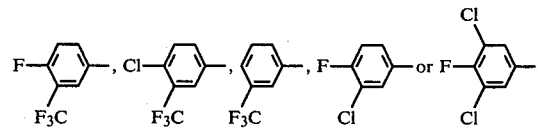

and both of $R^2$ and $R^3$ are lower alkyl.

* * * * *